(12) United States Patent
Pitts et al.

(10) Patent No.: US 6,230,050 B1
(45) Date of Patent: May 8, 2001

(54) METHODS AND APPARATUS FOR THE DETECTION OF DENTAL CARIES

(75) Inventors: Nigel Berry Pitts, Perth; Christopher Longbottom, Fife, both of (GB); Przemyslaw Los, Wroclaw (PL)

(73) Assignee: The University Court of the University of Dundee, Dundee (GB)

( * ) Notice: Subject to any disclaimer, the term of this patent is extended or adjusted under 35 U.S.C. 154(b) by 0 days.

(21) Appl. No.: 09/180,923

(22) PCT Filed: May 13, 1997

(86) PCT No.: PCT/GB97/01282

§ 371 Date: Aug. 5, 1999

§ 102(e) Date: Aug. 5, 1999

(87) PCT Pub. No.: WO97/42909

PCT Pub. Date: Nov. 20, 1997

(30) Foreign Application Priority Data

May 15, 1996 (GB) .................................... 9610101

(51) Int. Cl.[7] ............................................. A61B 5/04
(52) U.S. Cl. ...................... 600/547; 600/590; 128/734
(58) Field of Search ................................. 600/372, 382, 600/384, 386, 461, 476, 477, 478, 547, 590, 509; 128/734, 779; 364/414

(56) References Cited

U.S. PATENT DOCUMENTS

| | | | |
|---|---|---|---|
| 4,215,698 | 8/1980 | Nuwayser | 128/734 |
| 4,458,694 | * 7/1984 | Sollish et al. | 128/734 |
| 4,537,573 | 8/1985 | Sunada | 433/32 |
| 4,539,640 | * 9/1985 | Fry et al. | 364/414 |
| 5,086,781 | 2/1992 | Bookspan | 128/734 |
| 5,759,159 | * 6/1998 | Masreliez | 600/547 |
| 5,810,742 | * 9/1998 | Pearlman | 600/547 |
| 5,935,079 | * 8/1999 | Swanson et al. | 600/509 |

FOREIGN PATENT DOCUMENTS

| | | |
|---|---|---|
| 9305295 | 8/1993 | (DE) . |
| 4231386 | 3/1994 | (DE) . |

* cited by examiner

*Primary Examiner*—Tu Ba Hoang
(74) *Attorney, Agent, or Firm*—Ratner & Prestia

(57) ABSTRACT

The present invention is directed to a method and apparatus for the detection of dental caries. The method comprises the steps of placing at least one probe electrode in electrical contact with a surface of a patient's tooth, placing a second electrode in electrical contact with another part of the body of the patient, passing an alternating electrical current between said probe and second electrodes, and measuring the electrical impedance between the electrodes.

5 Claims, 4 Drawing Sheets

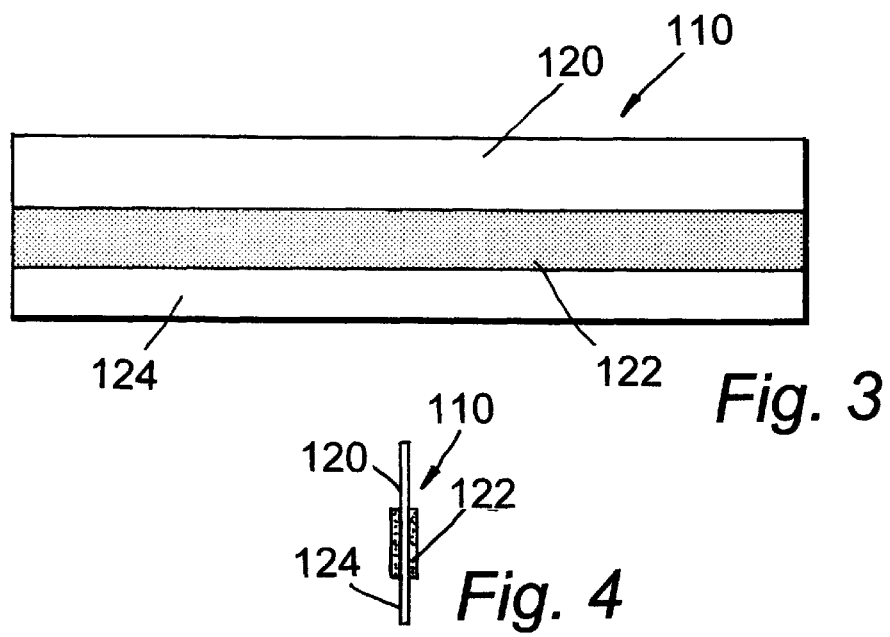
Fig. 3
Fig. 4
Fig. 5(a)
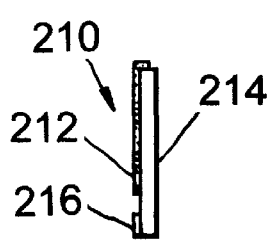
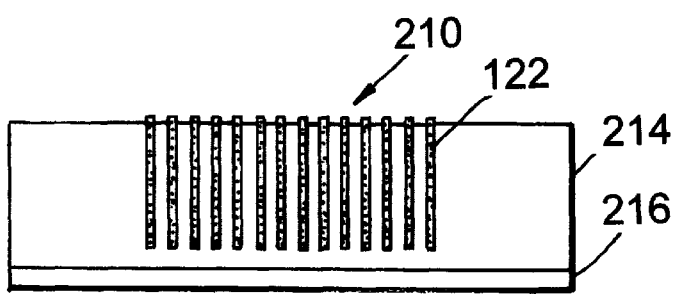
Fig. 5(b)
Fig. 6(a)
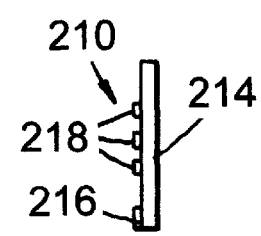
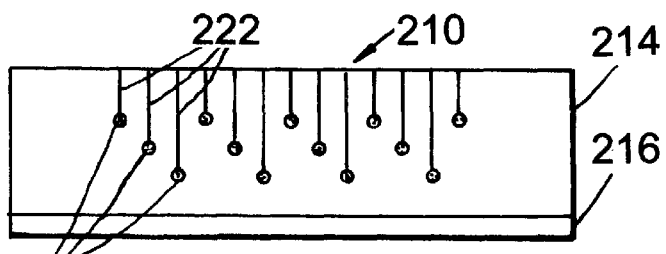
Fig. 6(b)
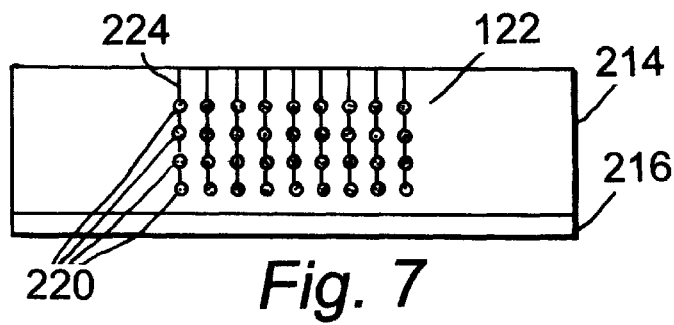
Fig. 7

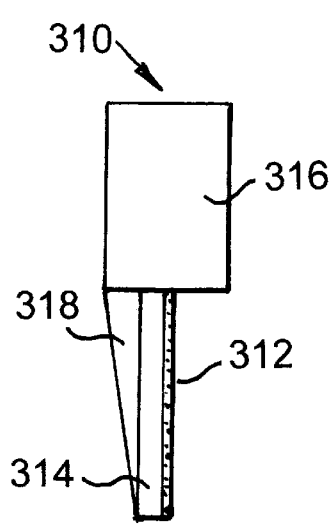
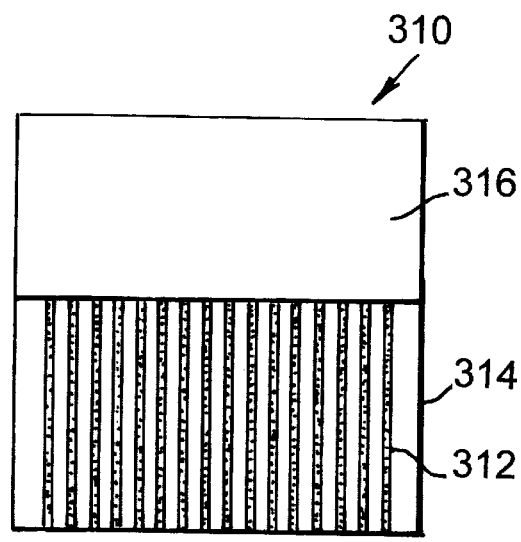
Fig. 8(a)                    Fig. 8(b)
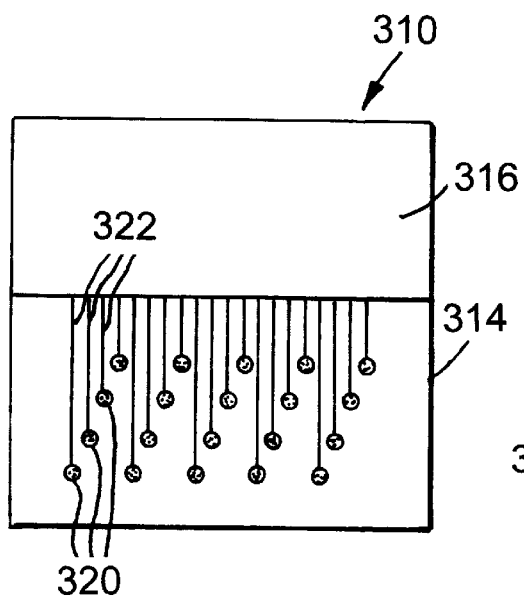
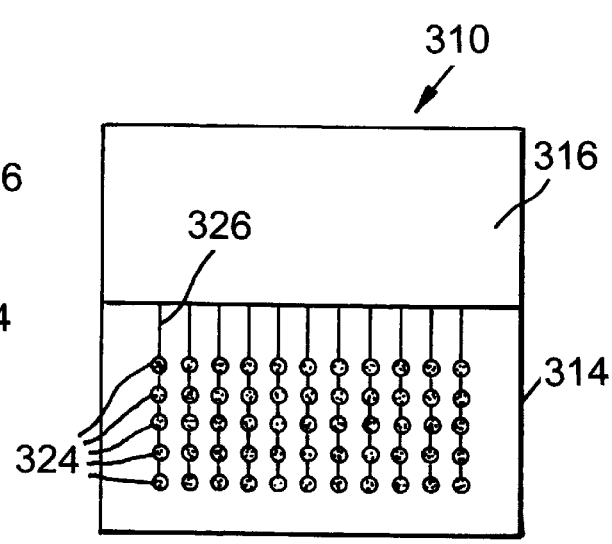
Fig. 9                       Fig. 10

METHODS AND APPARATUS FOR THE DETECTION OF DENTAL CARIES

BRIEF SUMMARY OF THE INVENTION

This invention relates to methods and apparatus for use in detecting dental carious (i.e. dental decay, or "caries" or "carious lesions") by electrical and/or electronic means.

BACKGROUND OF THE INVENTION

Caries is defined as the progressive decay of tooth or bone, and dental caries is the most common ailment known world wide. Dental caries can be treated by either removing the decayed material in the tooth and filling the resultant space with a dental amalgam, or in severe cases, by removal of the entire tooth.

The early diagnosis of dental caries is of utmost importance to any subsequent treatment since by the time pain is felt due to decay of the tooth, the treatment required to restore the tooth may be extensive and in some cases, the tooth may be lost.

Historically, the diagnosis of dental caries has been primarily visual, frequently accompanied by tactile examination using a mechanical probe. The patient may only seek an examination by a dental surgeon when in pain due to the caries and the surgeon must then identify the offending tooth by visual examination and/or by use of a mechanical probe which causes discomfort or pain in the decayed tooth. This experience is painful and distressing for the patient and acts as a disincentive to regular visits to the surgeon for routine examinations. In addition, the diagnosis of caries at this late stage of decay reduces the available options for treatment.

The diagnosis of caries by conventional techniques has become increasingly difficult. This is a result of several factors, including apparent changes in the morphology and in the rate of progress and distribution of carious lesions, as well as the inaccessibility of approximal (mutually contacting) dental surfaces and the complicated anatomy of pit and fissure sites on the occlusal (biting) surfaces.

An additional problem with conventional techniques is that decay on the approximal surface of the tooth resulting from plaque on the inter dental spaces may not be detected by simply prodding the tooth, since the approximal surfaces may not be reached by the probe. The limitations of conventional visual, tactile and radiographic diagnosis are well recognised. Decay may progress to an advanced stage on both occlusal and approximal sites without being detected until substantial tooth destruction has occurred.

In response to these generally unsatisfactory and unreliable methods of diagnosis attempts have been made to develop electrical/electronic means for the diagnosis of caries.

Electronic Caries Detectors (ECD's) generally comprise a probe having a first, probe electrode which is placed in contact with the tooth to be tested, and a second, counter electrode separate from the probe which is placed in contact with another part of the body of the patient in order to complete an electrical circuit connecting the two electrodes. The second electrode may be held by the patient or may be placed in contact against the gingiva (gum) or oral mucosa (inside cheek). An alternating electric current of fixed frequency is passed through the tooth and the resistance to this is measured. This electrical resistance has been found to correlate approximately inversely with the extent of caries in the tooth. The technique may involve measurement at a single point on the surface of the tooth, or the use of an electrically conductive paste, providing a measurement for the surface as a whole.

The configuration of conventional designs of ECD probes are such that they cannot contact approximal tooth surfaces, and therefore cannot detect approximal caries which does not extend to the occlusal or free smooth surfaces of the tooth. No satisfactory means to detect such approximal caries is currently known, although the problem of approximal caries has been prevalent for many years. Hitherto, the most accurate method of diagnosing approximal caries has been bitewing radiography, but this method is only about 30% accurate and requires the use of ionising radiation.

Even where good electrical contact can be established between the probe electrode and the relevant site, conventional ECD apparatus is of limited usefulness in the detection of caries.

DETAILED DESCRIPTION OF THE INVENTION

Among the objects of the various aspects of the present invention are the provision of: improved apparatus and methods for the electrical/electronic diagnosis of dental caries of all types; electrical/electronic probes for the detection of approximal caries; and improved electrical/electronic probes for the assessment of the occlusal and free smooth surfaces of the tooth.

In accordance with a first aspect of the invention there is provided a method for use in the detection of dental caries, comprising the steps of placing at least one probe electrode in electrical contact with a surface of a patient's tooth, placing a second electrode in electrical contact with another part of the body of the patient, passing an alternating electrical current between said probe and second electrodes, and measuring the electrical impedance between the electrodes to said electrical current; wherein the frequency of said alternating current is varied over a predetermined frequency range and the electrical impedance is measured for a plurality of frequency values within said range.

In the preferred embodiment of the invention, the impedance measurement and corresponding frequencies are analyzed by means of an alternating current impedance spectroscopy technique (ACIST) and a diagnosis of the tooth is based on the form of the impedance spectrum obtained thereby. The measurement frequencies are preferably in the range up to 500 kHz. Most preferably, the lower and upper frequencies in the range and the number of frequencies at which impedance measurements are made are selected on the basis of the type, size and configuration of the probe electrode(s), the specific tooth surface(s) and/or site(s) being contacted and whether or not the tooth has previously been restored (filled).

The probe electrode may comprise an array of miniature electrodes, enabling simultaneous or sequential impedance measurements to be made at multiple sites on one or more surfaces of the tooth.

Preferred forms of apparatus for use in the method, including preferred types of probe electrodes for approval and other tooth surfaces, are as defined below in relation to further aspects of the invention and as described more fully in the following description of embodiments of the various aspects of the invention.

In accordance with a second aspect of the invention, there is provided apparatus for use in the detection of dental caries, said apparatus comprising: at least one probe electrode adapted to be placed in electrical contact with a surface of a patient's tooth, a second electrode adapted to be placed in electrical contact with another part of the body of the patient, an alternating current source adapted for passing an alternating electrical current between said probe and second electrodes, and impedance measurement means for measuring the electrical impedance between the electrodes to said electrical current; wherein said alternating current source is a variable frequency alternating current source whereby the frequency of the alternating current applied to the tooth may be varied over a predetermined frequency range and the impedance measurement means is adapted to measure impedances corresponding to a plurality of frequency values within said range.

In accordance with a third aspect of the invention, there is provided a probe electrode device for use in the electrical/electronic detection of dental caries, comprising a substrate of electrically insulating material, and at least one electrode of electrically conductive material disposed on at least one surface of said substrate.

Preferably, said substrata comprises a generally planar, flexible, hydrophobic material, preferably PTFE, and most preferably Goretex. Where the device is intended for examination of approximal tooth surfaces, said substrate is sufficiently thin to fit between the approximal surfaces of adjoining tooth.

In certain embodiments of the third aspect of the invention, said at least one electrode comprises a layer of electrically conductive material applied to said substrate, preferably carbon impregnated PTFE, and most preferably carbon impregnated Goretex. In other embodiments, the electrodes comprise corrosion-resistant metal or other conductive material, such as carbon. The substrate may further include a strip of absorbent or hydrophobic material extending along at least one edge thereof.

In certain preferred embodiments, the probe device includes a plurality of electrodes located on said substrate. Said plurality of electrodes are preferably embedded in and project from said substrate. The electrodes may take the form of bands or disks, and are adapted for connection to the measurement circuit of a caries detection system either individually, collectively or in predetermined groups. The substrate is preferably connected to a holder/contact means, adapted to provide electrical connection between said electrodes and a measurement circuit. In one embodiment, the substrate is tapered in transverse cross section and includes a tapered core portion of compressible material, electrodes being provided on both opposite surfaces of said substrate.

Preferably, said plurality of electrodes are arranged in an array on said substrate. Most preferably, the width or diameter of said electrodes and the spacing between adjacent electrodes is in the range 0.5 $\mu$m to 200 $\mu$m.

In accordance with a fourth aspect of the invention, there is provided a dental caries detection system comprising apparatus in accordance with the second aspect of the invention and at least one probe electrode device in accordance with the third aspect of the invention. The system is preferably adapted to perform dental caries detection in accordance with the method of the first aspect of the invention.

Other aspects and preferred features of the invention are discussed in the following description of examples of the invention.

BRIEF DESCRIPTION OF THE SEVERAL VIEWS OF THE DRAWINGS

Embodiments of the invention will now be described, by way of example only, with reference to the accompanying drawings, in which:

FIG. 3 is a plan view of one side of an approximal probe electrode for use in a caries detection system such as that of FIG. 1, embodying a further aspect of the invention;

FIG. 4 is an end view of the electrode of FIG. 3;

FIGS. 5($a$) and 5($b$) are, respectively, end and front views of a first embodiment of a microprobe array embodying a further aspect of the invention;

FIGS. 6($a$) and 6($b$) are, respectively, end and front views of a second embodiment of a microprobe array embodying said further aspect of the invention;

FIG. 7 is a front view of a third embodiment of a microprobe array embodying said further aspect of the invention;

FIGS. 8($a$) and 8($b$) are, respectively, end and front views of a seventh embodiment of a microprobe array embodying said further aspect of the invention, configured for use on occlusal tooth surfaces;

FIG. 9 is a front view of an eighth embodiment of a microprobe array embodying said further aspect of the invention, configured for use on occlusal tooth surfaces;

FIG. 10 is a front view of a ninth embodiment of a microprobe array embodying said further aspect of the invention, configured for use on occlusal tooth surfaces;

Figure 1:
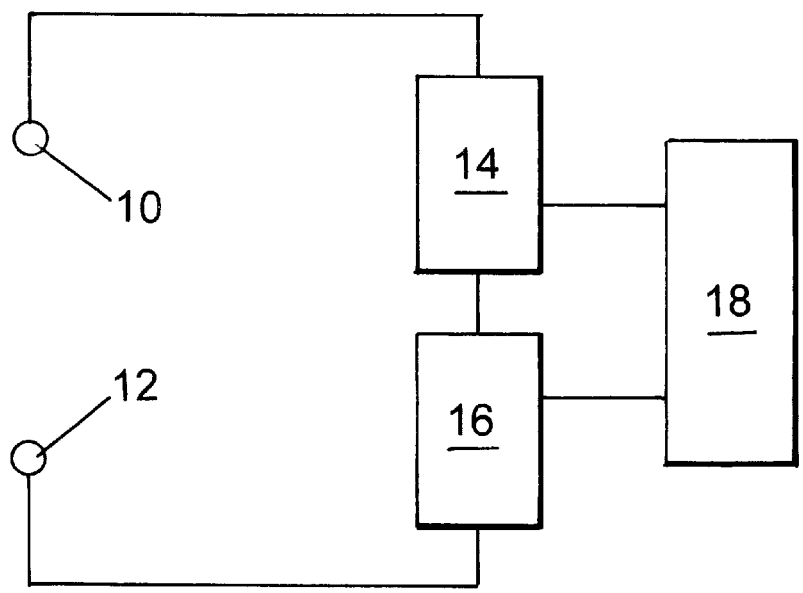
FIG. 1 is a schematic block diagram illustrating a caries detection system embodying the invention.

Referring now to the drawings, a basic caries detection system in accordance with the invention comprises a first "probe" electrode (or array of electrodes, as shall be discussed further below) 10, a second "counter" electrode 12, a variable frequency alternating current (a.c.) source 14 and impedance measurement means 16, connected in series as shown with an open circuit between the probe and counter electrodes, and data processing and control means 18 connected to receive data from the impedance measurement means 16 and to control the operation of the a.c. source 14.

The probe electrode 10 is adapted to be placed in electrical contact with the surface of the tooth which is to be examined and the counter electrode 12 is adapted to be placed in electrical contact with another part of the body of the patient, as discussed above, completing the circuit so that the impedance measurement means 16 measures the impedance between the two electrodes.

In use of the apparatus, the a.c. source 14 applies a predetermined voltage across the electrodes 10,12 so that the current flowing in the circuit varies with the impedance between the electrodes. This impedance is measured by the impedance measurement means 15. During examination of a tooth, the frequency of the a.c. source 14 is varied over a predetermined range and impedance measurements are recorded for a number of frequencies within the range.

The impedance measurements are analyzed by the data processing means. In accordance with the preferred embodiment of the invention the analysis comprises an a.c. impedance spectroscopy technique (ACIST). Suitably, the measurement frequencies are in the range up to 500 kHz. The lower and upper frequencies in the range and the number of frequencies at which impedance measurements are made may be selected on the basis of the type, size and configuration of the probe electrode(s), the specific tooth surface(s) and/or site(s) being contacted and whether or not the tooth has previously been restored.

The use of ACIST in detecting dental decay was tested using a sample of teeth consisting of 26 unrestored, extracted premolar teeth, with varying degrees of carious lesions in their approximal surfaces. The individual approximal surfaces were assigned to one of three groups on the basis of their direct visual appearance: sound (S) if no visible sign of caries was apparent; lesion (L) where white or brown spot lesions (indicative of demineralization due to caries) were evident with no detectable loss of surface enamel; and cavitated (C) if there was a carious lesion with an area where there was obvious lose of surface enamel. For each group, ten tooth surfaces were measured. Subsequent to measurement, the teeth were hemisectioned and serially sectioned to validate the visual categorisation of the teeth and to determine the true extent of any caries in enamel or dentine.

For these experimental purposes, the a.c. impedance measurements were carried out with the teeth placed in a custom-built perspex chamber. Each tooth was positioned in such a way that one of its approximal surfaces was facing an aperture in the chamber, through which the probe electrode, consisting of a stainless steel rod with a suitable electrically conducting material (discussed further below) at the tip, could be inserted to touch the surface of the tooth. A platinum counter electrode was used, the circuit being completed using K-Y lubricating jelly (Johnson & Johnson) as a conducting gel between the counter electrode and the root of the tooth. Each test tooth was held in wax at the base of the chamber.

Measurements were carried out using a computer-controlled Solartron Frequency Response Analyzer (FRA) 1255 connected to the cell via either a Solartron Potentiostat 1286 or EG&G 181 amplifier. The latter configuration was used for high impedance (>1 MΩ) measurements. Impedance measurements were carried out over a wide range of frequencies, typically from 300 kHz to 1 Hz. At least six measurements were carried out on each of the teeth to establish reproducibility of the results.

Figure 2:
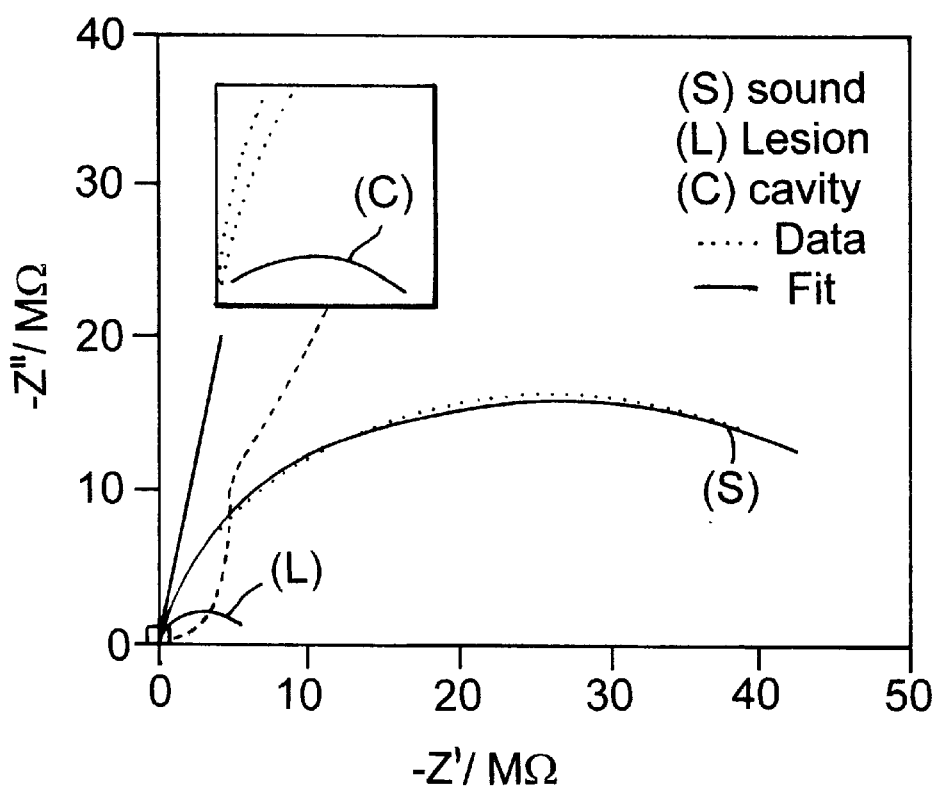
FIG. 2 is a graph showing plots of impedance values at varying frequencies for three sample teeth having different degrees of decay.

The results of the measurements of a representative tooth from each of the three categories S, L and C are shown in the graph of FIG. 2, where the impedance measured at each frequency for each of the three representative tooth samples are plotted on the complex plane. The values of the imaginary impedance Z" are plotted against the real impedance Z'. Three impedance "spectra" were thus obtained for the three sample teeth, labelled S, L and C on the graph. The plot for the group C tooth in enlarged in the inset, for clarity. The distance of each point from the origin of the graph represents the magnitude of the impedance and the angle subtended with the x-axis represents the phase angle θ.

The electrical response of any material can be represented by an equivalent electrical circuit consisting only of resistors and capacitors. In this particular case the equivalent circuit consists of four components: two resistors and two capacitors. The component representing the bulk resistance is connected in parallel with the capacitor representing the bulk capacitance. The second resistance is connected in parallel with a constant phase element, the impedance of which is given by $A\omega^{-n} - jB\omega^{-n}$, where A, B and n are constants and $\omega = 2\pi f$, where f is the frequency of the sinusoidally varying voltage.

The complex impedance data were analyzed using the computer program "Z Plot" (Solartron Instruments). A series of initial experiments were carried out to establish the contribution of the electrodes, gel, contacts and leads. These were found to be negligible in comparison with the impedance of the teeth.

The equivalent circuit derived for use in the experiments was fitted to the measurement data using a non-linear least-squares procedure. In FIG. 2, the solid lines represent the best fit obtained, and the dots represent the data. The scale of the differences in the in the electrical responses of the teeth in each of the three histological categories S, L and C is readily apparent.

The mean values (with standard deviations) for the total resistances in MΩ (the sum of the two resistances in the equivalent circuit), for each of the three groups were:

| | |
|---|---|
| Sound, S - | 53.47 (+/− 11.2) |
| Lesion, L - | 3.73 (+/− 2.58) |
| Cavity, C - | 0.31 (+/− 0.18). |

The impedance values for each of the three groups differ by an order of magnitude from the other two groups. The S group had values in the range 37–77 MΩ, compared with L group values in the range 0.9–10 MΩ and C group values in the range 76–559 kΩ.

Following the ACIST measurements, the approximal aspects of the teeth that were measured were photographed before hemisection of the teeth in the mesio-distal plane. The hemisections were examined under X2.5 and X10 magnification in a stereomicroscope, using reflected light, to assess the extent of caries. Photographs were taken of each hemisection and the teeth subsequently serially sectioned to produce 120 μm-thick sections, which were then viewed microscopically and scored for caries, and assigned to one of the groups S, L and C for comparison with the results of the ACIST analysis.

It can be seen from FIG. 2 that the impedance measurements for each of the three classes of teeth, S, L and C, fall into three quite distinct groups which corresponded exactly with the results of the subsequent microscopic examination of the teeth. Reproducibility of these results was excellent.

This study shows that the total, resistance of teeth as derived from a.c. impedance spectroscopy measurements is highly correlated with the presence and extent of decay in the teeth, as validated by histological examination.

The results show that the accuracy of the a.c impedance spectroscopy technique in this study was effectively 100%, in terms of both sensitivity and specificity.

The experimental technique used in this "in vitro" study can be transferred with minimal modification to "in vivo" use, thereby providing the basis for a system for clinical use having substantially higher accuracy than current methods of caries diagnosis.

The necessary a.c. source, impedance measurement means and control and data processing means may be integrated and/or packaged in any one of a number of ways for clinical use. It will be understood that the block diagram of FIG. 1 is primarily for illustrative purposes and does not necessarily reflect the physical arrangement of the components of a practical, clinical system.

Besides the basic methodology, hardware and software required to apply an ACIST approach to caries detection, the other main requirement for a clinical system is the provision of probe electrodes configured and optimised for "in vivo" use in order to enable examination of all of the relevant approximal, occlusal and free smooth surfaces of the teeth.

There will now be described a preferred embodiment of an approximal probe electrode in accordance with a further aspect of the invention.

Referring now to FIGS. 3 and 4, a probe electrode 110 for use in examining the approximal surfaces of teeth in an electrical/electronic caries detection system comprises an electrically insulating substrate 120 having an electrically conductive portion superimposed an at least a portion thereof and adapted to contact the approximal surface of a tooth when the substrate 20 is inserted between adjacent teeth.

In this example, the substrate 120 has conductive portions 122 on both sides thereof, allowing the approximal surfaces of two adjacent teeth to be examined without the need to remove and re-orient the substrate. In this example also, the substrate 120 is a generally elongate rectangle, and the conductive portions 122 comprise strips of conductive material extending along the length of the substrate 120 closer to one lateral edge thereof than to the other, but spaced from both lateral edges. The conductive portions 122 on either side of the substrate 120 are electrically isolated from one another.

In order to be suitable for clinical use, the electrode must be sufficiently thin, strong and flexible to be capable of being drawn between tightly abutting approximal surfaces of adjacent teeth, and must be hydrophobic and capable of being made electrically conductive at selected, specific locations.

A particularly preferred material meeting these criteria is polytetrafluoroethylene (PTFE), which is electrically insulating but which is capable of being selectively impregnated with conductive material. Most preferably, the PTFE comprises a material such as that manufactured and sold under the Trade Mark "Goretex".

In the illustrated example, the substrate 120 is formed from electrically insulating PTFE material, while the conductive strips 122 comprise layers of carbon impregnated PTFE secured to the substrate 120. The electrode is non-conductive in the area which will contact the gingiva, in use, (i.e. the lower lateral edge). The hydrophobic properties of PTFE aid electrical isolation of the conductive electrode area from oral fluids.

The probe electrode 110 in accordance with this aspect of the invention thus provides a means of making isolated electrical contact with the approximal surface of a single tooth, while providing electrical insulation between the electrode and the gum adjacent the tooth being tested. The probe electrode 110 may either be connected to a suitable, electrically conducting lead forming part of the circuit of FIG. 1, or else an electrode forming part of said circuit may be placed temporarily in contact with that part of the relevant conductive portion 122 of the probe electrode 110 which protrudes from between the teeth when measurements are to be taken, the counter electrode being held by the patient or being placed in contact with another portion of the patient's body distant from the tooth.

The configuration of the probe electrode 110 is such that electrical current is prevented from passing through adjacent teeth or through the gum, since the conductive material 122 of the electrode 110 is restricted to discrete areas on the substrate 120 and is insulated from the gum by the lower portion 124 of the non-conductive substrate.

Carbon impregnated PTFE was used, attached to the end of a stainless steel rod, for establishing electrical contact with the surfaces of the teeth in the experimental tests described above in relation to FIGS. 1 and 2. Initial "in viva" studies using an electrode in accordance with FIG. 3 produced results consistent with the "in vitro" study, indicating that the required electrical isolation of the conductive portions of the probe electrode from surfaces and fluids other than the surface under test is achieved in an "in vivo" situation.

Variations of the embodiment shown in FIGS. 3 and 4 might include the conductive portions 122 being restricted to specific areas, such as elliptical areas, on the substrate, with extensions of the conductive material leading to the upper lateral edge of the substrate 120 to allow connection to the circuit of the detection apparatus. Also, a fluid absorbing material might be attached along the lower lateral edge of the substrate 120 to absorb oral fluids and assist in the electrical isolation of the conductive portions 122.

There will now be described embodiments of a further probe arrangement in accordance with still another aspect of the invention.

This further aspect of the invention relates to the use of a probe device having a number of small probe electrodes ("microelectrodes" or "microprobes") arranged in an array. The microprobes may be formed from various possible conducting materials, such as metals which are corrosion resistant in the oral environment (e.g. platinum or gold) or carbon. The microprobes may take the form of wires, strips (bands) or disks, sealed or embedded in an electrically insulating carrier material. The microelectrodes may have a diameter in the range 1 $\mu$m to 100 $\mu$m. The carrier material may be rigid (e.g. glass) or may be formed from a thin, flexible material which can be brought into intimate contact with the surface of the teeth. Alternatively, the microprobes may have submicrometer dimensions (approximately $10^6$ active electrodes per square centimeter).

Microprobe arrays of this type may be used as the probe of an electrical/electronic caries detection system such as that of FIG. 1. The system may include computer software which transforms the results of the a.c. impedance measurements of the teeth into information regarding their health and internal structure.

The use of such arrays facilitates the analysis of the health and structure of the teeth with great precision (on the micrometer scale) taking into consideration the depth and the surface of the tooth being studied. This allows a three-dimensional (depth-surface) profile of the tooth to be obtained, thereby providing a map of the dental caries within the tooth and facilitating the provision of a very precise diagnosis of the health status of the tooth in a painless, safe and rapid manner (a few minutes per patient).

The arrays may include varying numbers of electrodes and may be configured for application to occlusal, approximal and free smooth surfaces of tooth crowns, as well as root surfaces, of both restored and unrestored teeth. The counter electrode may be placed on the unrestored or restored tooth and/or a restored portion of a restored tooth being measured, or on the oral soft tissues, or may be held in the hand of the patient.

Embodiments of such devices will be described with reference to FIGS. 5–13. It will be understood that these drawings are for illustrative purposes only, and the size, numbers and spacings of the microprobes may vary considerably from the illustrations. In particular, the microprobes may be substantially smaller in size, larger in number and more closely spaced. Typically, the width or diameter of the microprobes and of the spaces between adjacent microprobes might be in the range 0.5–200 μm.

The array design will vary according to the site being contacted and the material being used for the microelectrodes.

FIGS. 5(a) and 5(b) show an example of a microprobe array 210 configured particularly for use on approximal tooth surfaces. In this example the microelectrodes 212 comprise narrow bands embedded in a carrier body 214 of non-conducting material, such as resin. The microprobes 212 project from the "front" (tooth-contacting) surface of the carrier 214, typically by 1–100 μm, and extend to its upper edge for connection to the circuit of the detection apparatus.

The carrier 214 is generally planar and rectangular in shape, typically having a width of 10 mm and a thickness in the range 75–120 μm. The length of the carrier 214 is sufficient to accommodate the required microprobe array with spaces at either end to facilitate handling. The array of microprobes 212 might typically extend along a length of 5–10 mm of the central portion of the carrier 214. A strip of absorbent or hydrophobic material 216 extends along the lower edge of the carrier 214 to assist in isolating the microprobe array from the gum and oral fluids and also to act as a physical compressor. Preferably, this is a strip of PTFE (Goretex), which may be up to 50 μm in thickness and 1–2 mm in width.

FIGS. 6(a)–6(b) and 7 show alternative embodiments in which the microprobes comprise disks 218, 220 respectively. In FIGS. 6(a)–6(b), each microprobe 218 has an individual conductor 222 connecting it to the top edge of the carrier 214. In FIG. 7, the microprobes 220 are connected to the top edge of the carrier 214 in groups by conductors 224.

Microprobe arrays for use on free smooth tooth surfaces can be generally similar to the approximal devices shown in FIGS. 5(a)–5(b) and 6(a)–6(b), the overall dimensions of the carrier and of the actual array being varied to suit the surfaces in question.

Figure 11:
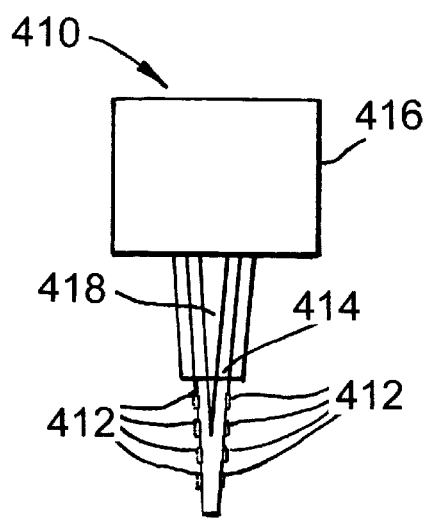
FIG. 11 is an end view of a tenth embodiment of a microprobe array embodying said further aspect of the invention, configured for use on occlusal tooth surfaces.

FIGS. 8(a)–8(b) to 11 illustrate embodiments of microprobe arrays configured for use on occlusal tooth surfaces.

In the example of FIGS. 8(a)–8(b), the device 310 comprises a non-conductive carrier 314 carrying an array of projecting band-type microelectrodes 312 similar to those of FIGS. 5(a)–5(b). The carrier 314 is typically about 40 μm in thickness and is connected along its top edge to a holder/contact-scanner unit 316 (described further below). A tapered block 318 of compressible material (preferably PTFE/Goretex) is secured to the carrier 314 on the opposite side thereof from the microprobes 312.

FIGS. 9 and 10 show variations of occlusal devices similar to the variants of FIGS. 6(a)–6(b) and 7. In FIG. 9, disk electrodes 320 are connected individually to conductors 322. In FIG. 10, groups of disk electrodes 324 are connected in groups by conductors 326.

FIG. 11 shows a further example of an occlusal device 410. In this case the non-conductive carrier 414 is tapered and has a central, tapered core 418 of compressible material (preferably PTFE/Goretex). The carrier 414 suitably tapers from about 80 μm to about 30 μm. Projecting microelectrodes 412 are located on both surfaces of the carrier 414, so as to contact the occlusal surfaces of upper and lower teeth simultaneously. The microelectrodes 412 may be of the band or disk type. In the latter case they may be arranged and connected as shown in either FIG. 9 or FIG. 10. The upper edge of the carrier 414 is again connected to a holder/scanner unit 416.

Figure 12:
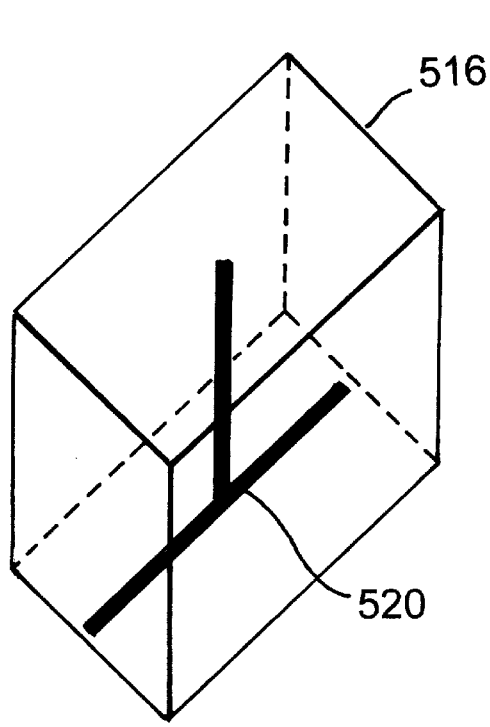
FIG. 12 is a schematic isometric view illustrating a first holder/contact unit for use with the microprobe arrays of FIGS. 5 to 13.
Figure 13:
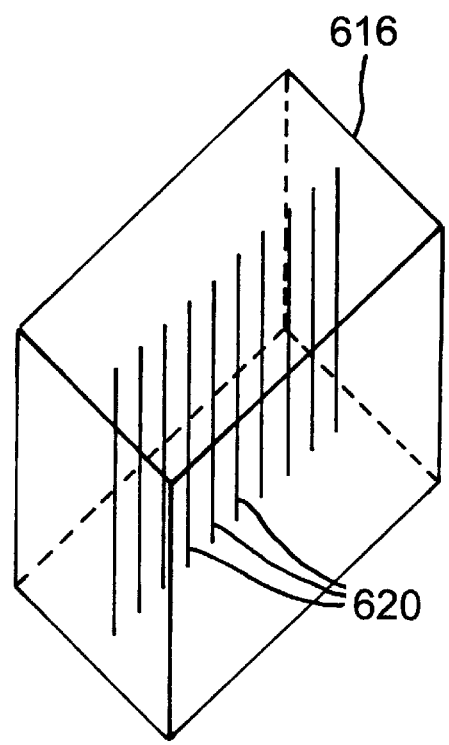
FIG. 13 is a schematic isometric view illustrating a second holder/contact unit for use with the microprobe arrays of FIGS. 5 to 13.

The holder/scanner units of FIGS. 8(a)–8(b) to 11 serve to facilitate handling of the devices and also provide means for connecting the various microelectrodes/conductors to the measurement circuit of the detection system. The devices may be configured such that all of the microelectrodes in the array are connected individually, or in groups or all in common. Where connected individually in groups, holder/scanner unit and/or the measurement circuit may include means for connecting each electrode or group into the circuit in turn for taking impedance measurements (i.e. for "scanning" the electrodes. FIG. 12 illustrates a holder/contact unit 516 in which a common "busbar" 520 is arranged to contact all of the microprobes/conductors of the array. FIG. 13 illustrates a holder/contact unit 616 in which individual conductors 620 are provided for connection to individual microelectrodes/conductors or groups of microelectrodes/conductors of the array. The choice of individual, group or common connection of the array can be made depending upon the type of information which is required from the examination.

For occlusal devices, the band or disk electrodes may be arranged in various configurations to facilitate electrical contact with the enamel of the pit and fissure pattern of the occlusal surfaces (which varies between individual teeth). The size of these occlusal arrays may vary in width, depth and thickness.

The computer software which processes the measurement data from the microprobe arrays may transform the impedance measurements into information showing analysis of the electrical resistance and capacitance of the measured tooth structure. This in turn is transformed, by means of an experimentally derived equivalent circuit, into information about the extent of mineralisation and surface integrity of the tooth structure, as previously described. The actual equivalent circuits derived will depend on the size and configuration of the microprobe arrays used. By means of the use of experimentally derived results for the electrical properties of sound and diseased tooth tissue at a submicrometer level, a computer program based on a developed three-dimensional model of tooth tissue at various specific sites may be used to transform the a.c. impedance data obtained during an examination into a three-dimensional (depth-surface profile of the tooth surface being measured. This may provide a map of the dental caries within the tooth, facilitating the provision of a very precise diagnosis of the health status of the tooth.

The system of FIG. 1 is advantageously used with one or more of the types of probe electrode device described with reference to FIGS. 3 to 13, providing a caries detection system which may provide a reliable, repeatable and accurate examination of all occlusal, approximal and free smooth surfaces of teeth "in vivo". Improvements and modifications may be introduced without departing from the scope of the invention.

What is claimed is:

1. A method for use in the detection of dental caries, comprising the steps of placing at least one probe electrode in electrical contact with a surface of a patient's tooth, placing a second electrode in electrical contact with another part of the body of the patient, passing an alternating electrical current between said probe and second electrodes, and measuring a electrical impedance between the electrodes to said electrical current; wherein a frequency of said alternating current is varied over a predetermined frequency range and the electrical impedance is measured for a plurality of frequency values within said range, wherein the probe electrode comprises an array of miniature electrodes, enabling simultaneous or sequential impedance measurements to be made at multiple sites on one or more surfaces of the tooth.

2. Apparatus for use in the detection of dental caries, said apparatus comprising: at least one probe electrode adapted to be placed in electrical contact with a surface of a patient's tooth, a second electrode adapted t o be placed in electrical contact with another part of the body of the patient, an alternating current source adapted to passing an alternating electrical current between said probe and second electrodes, and impedance measurement means for measuring the electrical impedance between the electrodes to said electrical current; wherein said alternating current source is a variable frequency alternating current source whereby the frequency of the alternating current applied to the tooth is varied over a predetermined frequency range and the impedance measurement means is adapted to measure impedances corresponding to a plurality of frequency values within said range, wherein said probe electrode comprises an array of miniature electrodes, enabling simultaneous or sequential impedance measurements to be made at multiple sites on one or more surfaces of the tooth.

3. A probe electrode device for use in the electrical-electronic detection of dental caries, comprising a substrate of electrically insulating material, and at least one electrode of electrically conductive material disposed on at least one surface of said substrate, wherein said substrate further includes a strip of absorbent or hydrophobic material extending along at least one edge thereof.

4. A probe electrode device for use in the electrical-electronic detection of dental caries, comprising a substrate of electrically insulating material, and at least one electrode of electrically conductive material disposed on at least one surface of said substrate wherein said probe electrode device includes a plurality of electrodes located on said substrate, wherein said plurality of electrodes are arranged in an array on said substrate, wherein the width or diameter of said electrodes and the spacing between adjacent electrodes is in the range of $0.5 \mu m$ to $200 \mu m$.

5. A probe electrode device for use in the electrical-electronic detection of dental caries, comprising a substrate of electrically insulating material, and at least two electrodes of electrically conductive material disposed on at least one surface of said substrate, wherein said substrate is tapered in transverse cross section and includes a tapered core portion of compressible material, said electrodes being provided on both opposite surfaces of said substrate.

\* \* \* \* \*

(12) EX PARTE REEXAMINATION CERTIFICATE (5935th)
United States Patent
Pitts et al.

(10) Number: US 6,230,050 C1
(45) Certificate Issued: Oct. 9, 2007

(54) METHODS AND APPARATUS FOR THE DETECTION OF DENTAL CARIES

(75) Inventors: Nigel Berry Pitts, Perth (GB); Christopher Longbottom, Fife (GB); Przemyslaw Los, Wroclaw (PL)

(73) Assignee: The University Court of the University of Dundee, Dundee (GB)

Reexamination Request:
No. 90/008,061, Jun. 1, 2006

Reexamination Certificate for:
Patent No.: 6,230,050
Issued: May 8, 2001
Appl. No.: 09/180,923
Filed: Aug. 5, 1999

(22) PCT Filed: May 13, 1997

(86) PCT No.: PCT/GB97/01282
§ 371 (c)(1),
(2), (4) Date: Aug. 5, 1999

(87) PCT Pub. No.: WO97/42909
PCT Pub. Date: Nov. 20, 1997

(30) Foreign Application Priority Data
May 15, 1996 (GB) ............................................. 9610101

(51) Int. Cl.
*A61B 5/05* (2006.01)
*A61B 5/103* (2006.01)
*A61B 5/117* (2006.01)

(52) U.S. Cl. ........................................ 600/547; 600/590
(58) Field of Classification Search ....................... None
See application file for complete search history.

(56) References Cited

U.S. PATENT DOCUMENTS 4,539,640 A * 9/1985 Fry et al. ..................... 600/547

OTHER PUBLICATIONS

An Abstract by Longbottom et al., published in Caries Research, 1993, No. 27, p. 207 and an accompanying presentation.*

Longbottom et al., "Detection of Dental Decay and its Extent Using A.C. Impedance Spectroscopy", Nature Medicine, vol. 2, No. 2, Feb. 1996, pp. 235–237.*

An abstract by Longbottom et al., published in regard to the conference proceedings of the 42$^{nd}$ ORCA Congress and an accompanying presentation.*

* cited by examiner

*Primary Examiner*—Beverly M. Flanagan

(57) ABSTRACT

The present invention is directed to a method and apparatus for the detection of dental caries. The method comprises the steps of placing at least one probe electrode in electrical contact with a surface of a patient's tooth, placing a second electrode in electrical contact with another part of the body of the patient, passing an alternating electrical current between said probe and second electrodes, and measuring the electrical impedance between the electrodes.

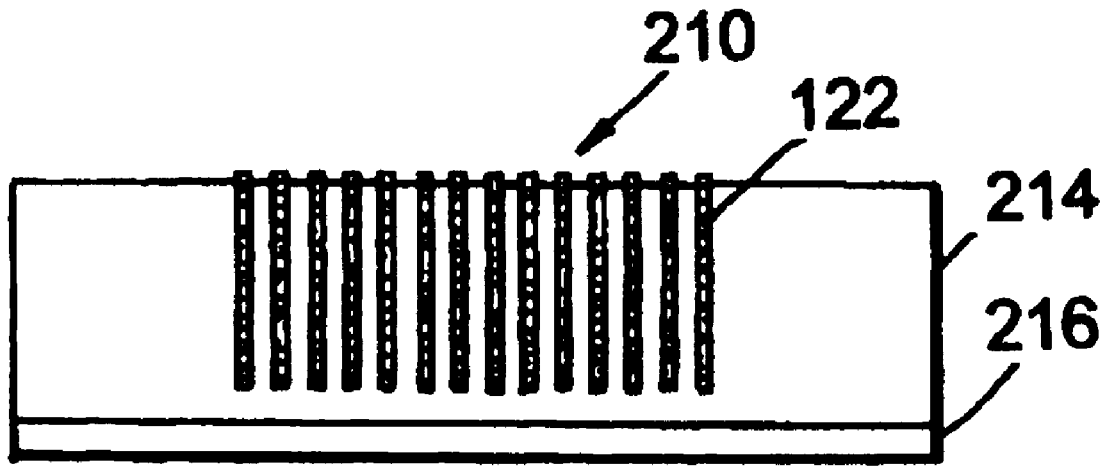

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1, 2, 4 and 5 is confirmed.

Claim 3 is determined to be patentable as amended.

3. A probe electrode device for use in the electrical-electronic detection of dental caries, comprising a substrate of electrically insulating material, and [at least one electrode] *a plurality of electrodes* of electrically conductive material disposed on at least one surface of said substrate, wherein said substrate further includes a strip of absorbent or hydrophobic material extending along at least one edge thereof.

* * * * *